(12) United States Patent
Klint

(10) Patent No.: US 6,502,606 B2
(45) Date of Patent: Jan. 7, 2003

(54) GUIDEWIRE

(75) Inventor: Henrik Sonderskov Klint, Lyngby (DK)

(73) Assignees: Cook Inc., Bloomington, IN (US); William Cook Europe ApS, Bjaeverskov (DK)

( * ) Notice: Subject to any disclaimer, the term of this patent is extended or adjusted under 35 U.S.C. 154(b) by 0 days.

(21) Appl. No.: 10/079,106

(22) Filed: Feb. 19, 2002

(65) Prior Publication Data

US 2002/0074051 A1 Jun. 20, 2002

Related U.S. Application Data

(62) Division of application No. 09/537,917, filed on Mar. 29, 2000, now Pat. No. 6,348,041.

(30) Foreign Application Priority Data

Mar. 29, 1999 (EP) .............................. 99610024

(51) Int. Cl.$^7$ ................................................ B21F 45/06
(52) U.S. Cl. .................................................... 140/71 R
(58) Field of Search ............................ 57/13; 140/71 R, 140/92.1

(56) References Cited

U.S. PATENT DOCUMENTS 2,072,284 A * 3/1937 Voorhees ........................ 57/13
2,107,810 A * 2/1938 Wherry .................... 140/71 R

* cited by examiner

*Primary Examiner*—Lowell A. Larson
(74) *Attorney, Agent, or Firm*—Brinks Hofer Gilson & Lione

(57) ABSTRACT

A guidewire (1) comprising a distal end (2), a shaft portion (4) and a proximal end (3), wherein the shaft portion comprises at least one helically wound group (10) of at least two wires (7,8,9) extending side by side and having a pitch angle in the range of 35° to 76°.

4 Claims, 3 Drawing Sheets

GUIDEWIRE

CROSS-REFERENCE TO RELATED APPLICATIONS

This is a Divisional of U.S. patent application Ser. No. 09/537,917 filed Mar. 29, 2000, now U.S. Pat. No. 6,348,041 which, in turn, claims priority to European Patent Application No. 99610024.4 filed Mar. 29, 1999 in the European Patent Office.

TECHNICAL FIELD

The present invention relates to the field of medical devices and more particularly to guidewires for vascular procedures.

BACKGROUND OF THE INVENTION

Medical guidewires for vascular procedures, such as angioplasty procedures, diagnostic and interventional procedures, percutaneous access procedures, or radiological and neuroradiological procedures in general, traditionally comprise an elongated core element with one or more tapered sections near the distal end thereof and a flexible helical coil disposed about the distal portion of the core element. The distal extremity of the core element or a separate safety ribbon which is secured to the distal extremity of the core element extends through the flexible coil and is secured to the distal end member of the guidewire, which is a rounded member at the distal end of the helical coil. Torquing means are provided on the proximal end of the core element to rotate and steer the guidewire while it is being advanced through a patient's vascular system.

The physician views the progress on a screen and makes the distal end of the guidewire enter and follow tortuous vascular vessels from the entry site through the various vascular branches to the target site by pushing and rotating the proximal end of the guidewire outside of the patient. In connection with the advancement of the guidewire or once the guidewire has been positioned at the desired site, a wide variety of medical devices may be directed to the target site along the guidewire by simply sliding the device over the guidewire and advance the device to the distal end of the guidewire. A typical medical device is a catheter, and very often a catheter and the guidewire are introduced in a common procedure where the guidewire is advanced a distance in front of the catheter, then the catheter is advanced over the guidewire, followed by a further advancement of the guidewire. Following placement of the catheter or other device, the guide wire can be removed if desired.

The flexible coil acts as a protective measure of a suitably large diameter, hindering the guidewire core in damaging the vascular wall. The above mentioned guidewire is known from U.S. Pat. No. 4,619,274 to Morrison whose guidewire has a progressively attenuated diameter. An elongated core element extends from the proximal to the distal ends of the guidewire and has a decreasing cross sectional area in a direction towards the distal end member. A coil is carried by and secured to said core element and has proximal and distal ends. The coil has a diameter which decreases in a direction towards the distal end. The coil is formed of a single helical wound wire which has a diameter which decreases from one end to the other end with the larger diameter beginning in a region closer to the proximal end and the smaller diameter wire ending in a region closer to the distal end.

U.S. Pat. No. 5,001,825 to Halpern describes a fabrication process for a guidewire core where a solid metal wire is drawn down in several stages to have a stepwise decreasing diameter towards the distal end. The core is surrounded by a flexible coil having an outer diameter which decreases near the distal end. The coil consists of a single helical wound wire having a constant cross sectional area.

It is an object of the present invention to provide a guidewire which in its distal area is highly flexible and yet capable of transferring torques applied to the proximal end of the guidewire to the distal end of the guidewire in a very precise manner even when the guidewire follows a loop-shaped course.

SUMMARY OF THE INVENTION

The present invention relates to a guidewire comprising a distal end member and a shaft portion extending in a longitudinal direction from a proximal end towards the distal end member, and at least one helical wound wire extending from a position at the shaft portion to the distal end member. In view of this, the guidewire according to the present invention is characterized in that at least one helical wound group of at least two wires extending side by side has a pitch angle in the range of 35°–76°.

In the prior art guidewires the core element transfers the torque to the distal area of the guidewire, but the core element also restricts the flexibility of the guidewire. When the core element is given a very small diameter in its distal area in order to improve the flexibility, it loses the ability to transfer the torque. When, according to the invention, the flexible coil in the distal end of the guidewire is made of two or more wires which are wound with a pitch angle in the specified range, the wound wires transfer torque and also force components directed in the axial direction of the guidewire to the distal end thereof.

The guidewire surprisingly maintains its capabilities for transferring torque when it follows a tortuous path involving two or more loops. The torque is transferred all the way to the distal end member or tip of the guidewire, meaning that the distal end member can be very precisely steered from the proximal end. If the pitch angle exceeds 80° the ability to transfer torque is lost.

In a preferred embodiment, along a distance of at least 10 cm from the distal end member said at least one helical wound group of wires is the primary or the sole torque-transferring means between the shaft portion and the distal end member. Because the torque is transferred through the helical wound wires the central core can be given very feeble dimensions, thus increasing the flexibility of the distal portion, or it can be completely left out by making at least the most distal 10 cm of the guidewire without a torque-transferring solid metallic core inside said at least one group of wires. If desired there can be a safety ribbon inside the wound wires, connecting the rounded distal end member with a more proximal shaft portion, but such a ribbon will normally not be required.

Due to the very high flexibility, pushability and torquability and the ability of the guidewire to maintain each of these three characteristics even when set in a very tortuous pattern involving two or more tight loops the guidewire can be of use in very small and distant vessels. In order to further enhance use of the guidewire in vessels with small lumen the at least one helical wound group of wires has a smaller outer diameter at the distal end than at said position on the shaft portion.

If the group of wound wires is secured to the shaft, which for example can be of traditional type with a core member or can be another group of wires of larger dimensions, such as by soldering or welding the proximal end of the group onto the shaft the guidewire can be prone to kinking at the transition between the flexible group of wires and the remainder of the shaft. With a view to avoiding this, the said at least one helical wound group of wires preferably extends into the shaft portion towards the proximal end, and even more preferably it extends along a guidewire length at least in the range of 20–50 cm from the distal end. The additional stiffness caused by the attachment of the wire is less disturbing the longer it occurs from the distal end of the guidewire. It is possible to let the group or groups of helical wound wires extend to a position at the proximal end of the guidewire, so that they span the entire guidewire. It is preferred that the wires in said at least one group have a separation from one wire to the next in the group of less than the diameter of the wire. Normally, the wires in the group are placed so close they touch each other.

In one embodiment the at least one of the wires in said at least one group is ribbon-shaped. The widest cross sectional dimension, the breadth of the wire is directed in the longitudinal direction of the guide-wire. It is preferred that the ribbon-shaped wire has rounded edges.

In a preferred embodiment the at least one group of wires is made of from 2 to 8 helical wound wires. A number of the wires are placed next to each other and winded in the same direction. By using several wires their aggregate breadth can be adapted to correspond to the desired pitch distance. As an alternative to winding all wires in the same direction some, such as one half of the number of wires, can be winded in one direction while others, such as the other half, can be winded in the opposite direction. Such winding can be effected in separate rounds resulting in a coil of two layers of wires with mutual opposite handedness.

In the preferred embodiment the guidewire is made without a solid or hollow metallic core inside the at least one coil. By dispensing with the metallic core the flexibility of the guidewire is increased, and the manufacturing of the guidewire is simplified.

In an embodiment the cross-section of said wires in said at least one helical wound group is a circular shape in the proximal end of the wire, and in the distal portion of the wire the cross-section has the shape of a circular segment which has a straight line facing radially outwards. Such a variation of the cross-sectional shape can be the result of grinding of a helical wound wire on its outside with the purpose of reducing the diameter of the helical wound wire in its distal portion. The circular segment has less cross sectional area than the corresponding full circular, shape, and the reduced cross-sectional area greatly increases the bending flexibility of the helical wound wire without sacrificing its ability to transfer torque.

In another aspect the present invention relates to a guidewire comprising a distal end, a shaft portion and a proximal end, wherein the shaft portion comprises at least one helical wound group of at least two wires having a pitch angle in the range of 35°–72°, and said at least one helical wound group of wires having said pitch angle extends to the distal end of the guidewire. With this guidewire the above mentioned advantages are achieved.

The present invention further relates to a method of manufacturing a guidewire, wherein a guidewire body is provided, said body comprising at least one helical wound group of at least two wires having a pitch angle in the range of 35°–76°, wherein an elongate distal guidewire portion of said at least one helical wound wire is subjected to grinding reducing the outer diameter of said distal guidewire portion in relation to a proximal portion of the guide wire. Grinding is an advantageous manner of manufacturing the above mentioned guidewires because it is very easy to adapt the grinding process to the specific guidewire to be produced, and a wide variety of guidewires can be premanufactured as wound guidewire bodies having an even outer diameter along their entire length. When the specific use of the guidewire is specified, such as a guidewire for accessing a kidney in an adult via the femoral route, which requires a guidewire having a relatively long portion with the full diameter and a relatively short portion with a quickly reduced diameter, or a guidewire for neuroradiological use via the femoral route, which requires a gentle reduction in diameter over a relatively long distance and a long and soft distal portion, it is a simple matter to adjust the grinding process to the desired guidewire.

The method can be adjusted to grind the elongate distal portion of the guide wire to have a substantially continuously diminishing outer diameter which results in a gradual increase of bending flexibility of the guidewire.

It is further possible to adjust the method to grind the elongate distal portion of the guide wire to have a substantially stepwise diminishing outer diameter which is often preferable in case of very long distal portions. Further, the method can be so that elongate distal portions of the guide wire are ground to have areas with diminishing outer diameters mixed with areas having substantially constant outer diameters.

BRIEF DESCRIPTION OF THE DRAWINGS

Examples of the invention will now be described in more detail with reference to the highly schematical drawings, in which.

DETAILED DESCRIPTION

Figure 1:
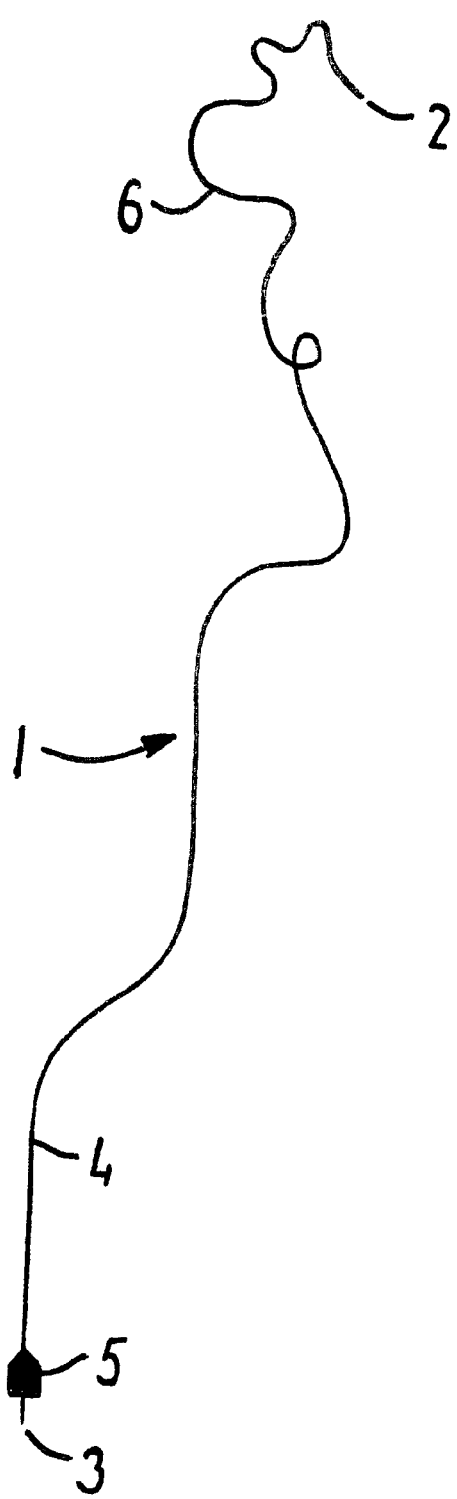
FIG. 1 depicts a sketch of a guidewire according to the invention when following an example of a course in the vascular system.

In the following description of the embodiments, the same reference numerals are used for features of the same type.

A guidewire seen in FIG. 1 is generally denoted by 1 and has a distal end 2 capable of being advanced to a target site in the vascular system and a proximal end 3 that is kept outside the patient's body. A shaft portion 4 extends from the proximal end towards the distal end and carries near the proximal end a handle 5 releasably secured to the guidewire. The guidewire can typically have a length in the range of 50–300 cm and a maximum outer diameter in the range of 0.204–1.072 mm (0.008–0.042 inches). It can also include several segments where the proximal segment has a larger diameter than one or more intermediate segments which has/have larger diameters) than the distal segment. When such a guidewire follows a tortuous vessel path involving several sharp bends, loops and the like, it is desirable that a turning of handle 5 results in a similar turning of the distal end 2.

The shaft portion 4 can include a solid shaft which is of a metallic material such as medical grade stainless steel or Nitinol. In that case a coiled distal portion 6 is fixed onto and in extension of the shaft portion. However, in the preferred embodiment the coiled portion continues from the distal to the proximal ends, and the use of a solid shaft is made superfluous. The coiled portion ends distally at the distal end member 2, which is a member having a soft front end termination, such as a rounded front or a front of very flexible material or very flexible configuration. End member 2 can be a solder, or a sphere that can be laser welded, for example, onto the distal end of the coiled portion. Further, end member 2 can also include a soft coil of radiopaque material. In the embodiment depicted in FIG. 2 three wires 7, 8 and 9 have been placed next to each other and have been wound in a common operation into a wound group of three wires 10 with a pitch angle $\alpha$ of the individual wire of about 40°. The pitch angle is the included angle between the longitudinal axis of the guidewire and the center axis of the relevant wire 7, 8 or 9. The size of the pitch angle depends on the diameter of the wire, the diameter of the guidewire, and of the number of wires in a group. If the pitch angle is smaller than 35° the desired torquability is lost, and if the pitch angle becomes larger than 76° it also becomes difficult to transfer the torque to the distal end. The most preferred pitch angle is in the range of 50 to 70°. A pitch angle in the ranges of 35–50° or 70–76° is also to the properties of the guidewire. If the pushability is the most important criteria the pitch angle can be chosen at for example 38°, and if the bending flexibility is most important the pitch angle can be chosen at 75°, for example. However, the combination of torque transferral, pushability and transverse flexibility is normally well-balanced for pitch angles in the range of 50–68°. The pitch or pitch distance is indicated by b and is the distance in the longitudinal direction of the guidewire from the first wire in one turn of the group to the same first wire in the next turn of the group.

The wire 7, 8 or 9 is of a linear elastic material, such as stainless steel, titanium or tantalum, or it is made of a superelastic alloy, such as Nitinol. The diameter d of the wire is in the range of 0.06–0.45 mm, and preferably in the range of 0.150.35 mm. In case the wire is of stainless steel it has preferably an ultimate tensile strength in the range of 1800–2700 N/mm$^2$ but lower or higher values are also possible. The guidewire is made by placing a group of from two to eight wires in a row next to each other, such as according to the desired pitch angle, where after the group of wires is wound about a mandrel. Then the mandrel with the coiled wires can be subjected to heat treatment in order to remove residual stresses from the wires. As an example, the heat treatment can last for about two hours in an oven at a temperature of about 500° C. After the heat treatment the mandrel is removed from the wires.

Figure 2:
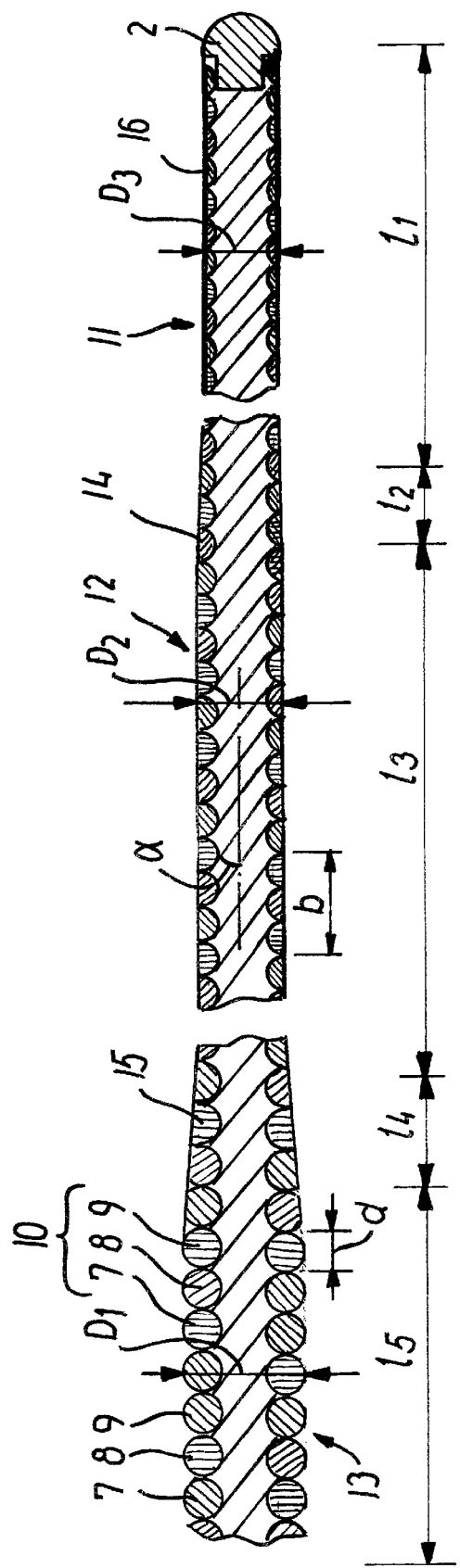
FIG. 2 illustrates a partial, longitudinal section through an embodiment of the guidewire.

In the embodiment shown in FIG. 2 the distal portion 6 has a plurality of sections 11, 12 and 13 having sequentially smaller outer diameters D1, D2 and D3 towards distal end member 2 with tapered sections 14 and 15 connecting the smaller diameter sections with larger diameter sections. The sections with reduced diameter have been manufactured by grinding the distal portion in a centerless grinding machine. The inner diameter of the sections 11–13 is preferably constant.

In the ground portions, wires 7, 8, 9 have a cross-section that deviates from a circular shape and have the shape of circular segment which has a straight line 16 facing radially outwards. In the shaft portion the guidewire has a diameter D1 corresponding to the diameter of coil 10 prior to its grinding where the wires 7, 8 and 9 have their full cross-sectional area. This diameter is present along the length 15.

The three wires placed in a group side by side are identical. The grinding procedure produces the tapered section 15 in which the outer diameter diminishes to diameter D2, and the tapered section 14 in which the outer diameter of the guidewire diminishes to diameter D3. Due to the smaller outer diameters sections 13 and 11 have considerably larger transverse flexibility and higher softness, but torque is nevertheless surprisingly transferred fully to the distal end.

Figure 3:
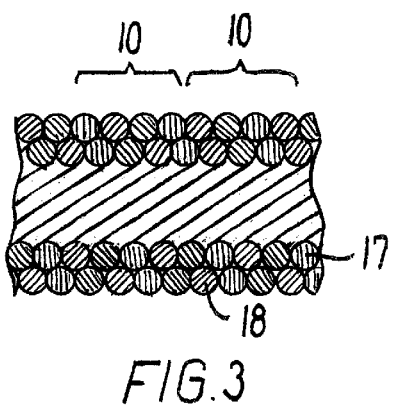
FIGS. 3–5 depict partial, longitudinal sections through helical wound wires in embodiments of the guidewire.
Figure 4:
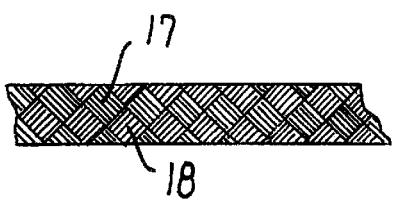

The guidewire can in part or along the entire length include two rows of wires placed one outside the other as illustrated FIG. 3. The inner row 17 includes a group of wires wound in the opposite direction than the group of wires in the outer row 18. In case the proximal portion of the guidewire is to have a large stiffness in order to be able to be directed through large vessel over long distances it can be an advantage to utilize at least two rows of wires in the proximal portion and less rows or a single row in the intermediate and/or distal portions of the guidewire. As an alternative to be placed one outside the other the groups of wires can be braided as illustrated in FIG. 4 which results in more homogenous properties of the guidewire but also in somewhat less flexibility.

Figure 5:
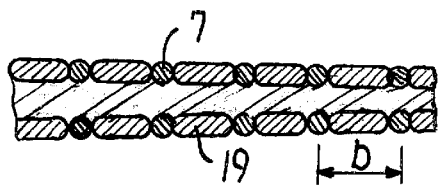

In the embodiment of FIG. 5 the group of wires includes a single ribbon-shaped wire 19 and a wire 7 with circular cross-section.

If a particular flexible design is desired without sacrifice to torquability each wire in a group can be braided or layered of several filaments or strands each having a diameter in the range of 0.01–0.10 mm, using traditional lay patterns and methods known from the making of ropes and wires.

Figure 6:
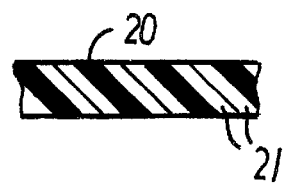
FIGS. 6–9 depict partial, longitudinal views of embodiments with a radiopaque marker in the distal end.
Figure 7:
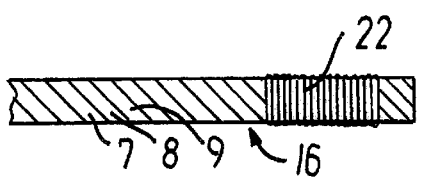

In order to make the tip portion of the guidewire more visible on a screen it is desirable to use some kind of radiopaque material, such as platinum which in itself lacks the desirable high strength properties provided by the use of stainless steel, Nitinol or another material of high strength and large flexibility and elasticity. In the embodiment illustrated in FIG. 6 by a sectional view of the distal portion, one wire 20 or strand out of a group of three is of the radiopaque material and the remaining two 21 are out of the high strength material. The wire 20 can have a relatively short length and be fixed in distal extension of, a wire of the same type as wires 21.

Figure 8:
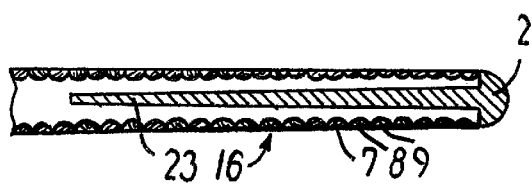
Figure 9:
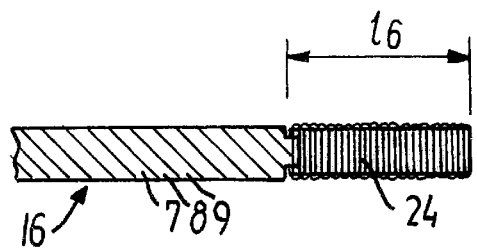

As an alternative, a guidewire distal portion 16 of the type shown in FIG. 2 can be provided with a coil 22 of radiopaque wire which has a very small wire diameter, such as 0.05–0.35 mm. The coil has a pitch distance corresponding to the diameter of the wire, and consequently coil 22 is unable to transfer torque and is very flexible so that the desired properties of the distal guidewire portion are not impaired by adding coil 22 to the guidewire. Another embodiment according to the invention is outlined in FIG. 8 where tip 2 is of radiopaque material and includes a thread or a ribbon 23 of similar material that extends centrally into the hollow inner space in the guidewire to a free end. Further it is possible to position a distal tip member designed as a very soft coil 24 of radiopaque material in extension of wires 7, 8, 9 as outlined in FIG. 9. Such a coil can for example have a length 16 of about 35 mm. Apart from making the tip visible it can also serve as a very soft and pliable tip member.

The guidewire can be made with a uniform diameter throughout its length. In case the guidewire has a diminishing diameter toward the distal end, a prefabricated guidewire of uniform diameter can be ground to the diesired dimensions as described above. The grinding removes material from the outwardly facing portions of the wire or wires of the distal end portion, as seen in FIG. 2.

As an alternative or supplement to grinding, the guidewire can be composed of several wire portions in which the wires have mutually different diameters and cross-sectional areas. In a proximal portion the wires can have a larger diameter than the wires in one or more intermediate portions and these can have larger diameter than the wires in a distal portion.

In the following, some examples of guidewires made according to the invention are described.

EXAMPLE 1

Wires of stainless steel grade AISI 304 and an outer diameter d=0.014' (0.35 mm) were used for making guidewires. Two lengths of wires were placed side by side in a group which was wound about a mandril resulting in a guidewire which had an outer diameter of D=0.042" (1.07 mm), where after the mandril was removed. The same was repeated with groups of three, four and five wire lengths placed side by side and wound in a common movement around the mandril. The resulting wires were placed in loop-shape with a number of loops having an approximate loop diameter of 2 cm and the ability to transfer torque from one end of the wire to the other was visually examined. Then the pitch angle was visually determined under 50 times magnification. This manner of determining the angle is somewhat inaccurate but provides a rough estimate of the angle. There was also made a coil of a single wire. The single wire coil had a pitch angle of about 80° and it was unable to transfer torque when it had two loops. The guidewire made of a group of two wires had a pitch angle of about 72°, and it could transfer torque when set with two loops and three loops. The guidewire made of a group of three wires had a pitch angle of about 64° and it transferred perfectly the torque in a 1:1 relationship even when set with three or more loops (ten loops functioned). The guidewire made of a group of four wires had a pitch angle of about 53° and turned out to have the same excellent properties as the one with a group of three wires. The guidewire made of a group of five wires had a pitch angle of about 40° and turned out to have the same excellent properties as the one with a group of three wires. The higher number of wires provides the shaft less flexibility and larger pushability, which can be desirable for guidewires used for passing long distances through larger vessels.

EXAMPLE 2

With wire lengths having a diameter of d=0.008" (0.20 mm) a group of four wires was wound around a mandril as described above, and a pitch angle of about 52° was determined in the resulting guidewire which had an outer diameter of D=0.63 mm (0.025"). The guidewire was tested like mentioned above and it showed excellent properties. Torque could be transferred even when the guidewire was set with more than 10 loops.

EXAMPLE 3

With wire lengths having a diameter of d=0.003" (0.075 mm) groups of two and three wires were wound around a mandril as described above, and pitch angles of about 66 for the three wire group and about 76° for the two wire group were determined in the resulting guidewire which had an outer diameter of 0.010" (0.25 mm). The guidewires were tested like mentioned above, and the one with the two wire group could transfer torque, but not as well as in Example 2, and the one with the three wire group could without problems transfer torque when set with three loops.

EXAMPLE 4

With wire lengths having a diameter of d=0.006" (0.15 mm) a group of four wires was wound around a mandril as described above, and a pitch angle of about 50° was determined in the resulting guidewire which had an outer diameter of D=0.018" (0.45 mm). The guidewire was tested like mentioned above and it showed excellent properties. Torque could be transferred even when the guidewire was set with more than 10 loops. The various embodiments can be combined into other embodiments within the scope of the present invention. Other modifications are possible, such as using a core member within the coiled wires, which core member can extend along the proximal and any intermediate portions but not along the distal portion. The core member can have a cross-sectional area that diminishes gradually or stepwise at increasing distance from the proximal end of the guidewire.

What is claimed is:

1. A method of making a guidewire, comprising the steps of:
   winding as a group at least two wires side-by-side about a mandril at a pitch angle in the range of 35° to 76°, in helical fashion to define a lumen therewithin, thus forming a guidewire having a distal end portion and a proximal end portion; and
   reducing the diameter of the outer surface of the distal end portion of the guidewire to be less than that of the proximal portion of the guidewire.

2. The method as set forth in claim 1, wherein the pitch angle is in the range of 35° to 72°.

3. The method as set forth in claim 1, wherein the step of reducing the outer diameter of the distal end portion comprises grinding the outwardly facing portions of the helical wound wires that form the distal end portion.

4. The method as set forth in claim 1, wherein the wires being wound have gradually changing diameters, and the group of withers is wound to have a constant inner diameter.

* * * * *

UNITED STATES PATENT AND TRADEMARK OFFICE
CERTIFICATE OF CORRECTION

PATENT NO.    : 6,502,606 B2
DATED         : January 7, 2003
INVENTOR(S)   : Henrik S. Klint It is certified that error appears in the above-identified patent and that said Letters Patent is hereby corrected as shown below:

<u>Title page,</u>
Item [30], Foreign Application Priority Data, delete "99610024" and substitute -- 99610024.4 -- in its place.

Signed and Sealed this

Seventh Day of October, 2003

JAMES E. ROGAN
*Director of the United States Patent and Trademark Office*